United States Patent [19]

Schmid et al.

[11] Patent Number: 5,060,637
[45] Date of Patent: Oct. 29, 1991

[54] DISPOSABLE CERVICAL COLLAR

[75] Inventors: K. Stephen Schmid, New Vienna, Ohio; Richard A. Brault; Dianne B. Croteau, both of Toronto, Canada; Jonathan P. Vinden, Mississauga, Canada

[73] Assignee: Ferno-Washington, Inc., Wilmington, Ohio

[21] Appl. No.: 143,006

[22] Filed: Jan. 12, 1988

[51] Int. Cl.⁵ .............................................. A61H 1/02
[52] U.S. Cl. .............................. 128/75; 128/DIG. 23
[58] Field of Search ................ 128/75, DIG. 23, 87 B

[56] References Cited

U.S. PATENT DOCUMENTS 3,916,884 11/1975 Attenburrow ............... 128/DIG. 23
4,325,363 4/1982 Berkeley ...................... 128/DIG. 23
4,712,540 12/1987 Tucker et al. ........................ 128/75

Primary Examiner—Edgar S. Burr
Assistant Examiner—Aaron J. Lewis
Attorney, Agent, or Firm—Frost & Jacobs

[57] ABSTRACT

A disposable cervical collar having an elongated unitary body formed from plastic core board or similar cellular material, the collar having a frontal section provided with a chin receiving opening, including a chin supporting flap and optionally a chin strap, with a throat opening underlying the chin opening, and a rear section which is slotted at spaced intervals for bending to conform to the wearer's neck, the rear section having a plastic strap adapted to be adhesively secured to the frontal section to secure the collar in place.

11 Claims, 2 Drawing Sheets

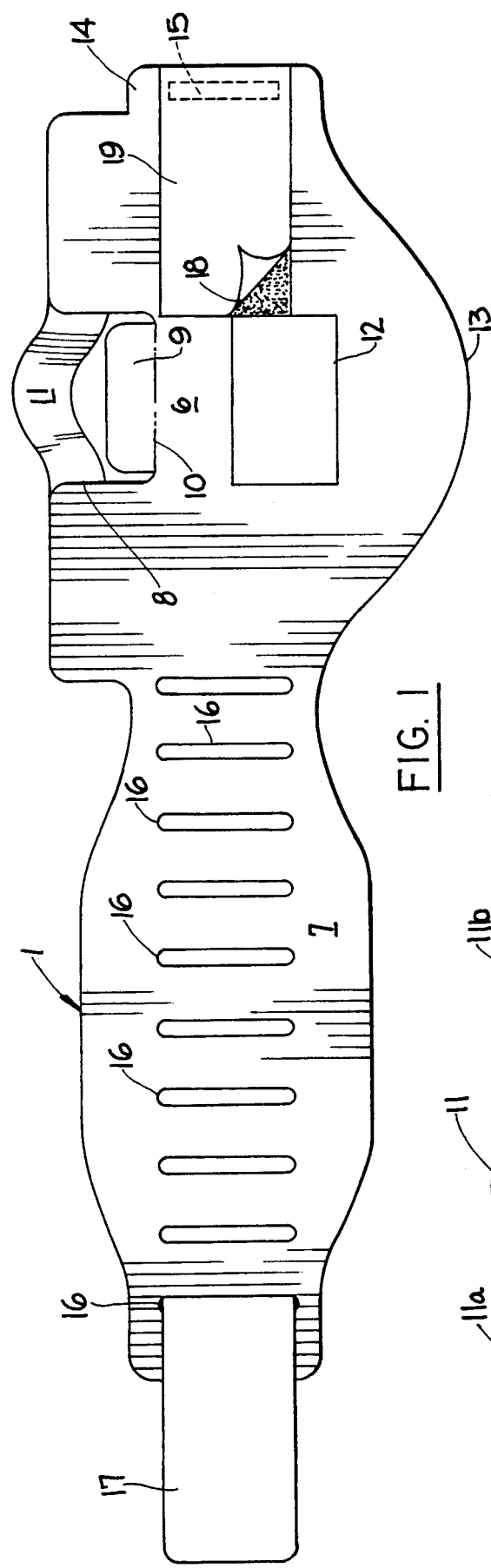
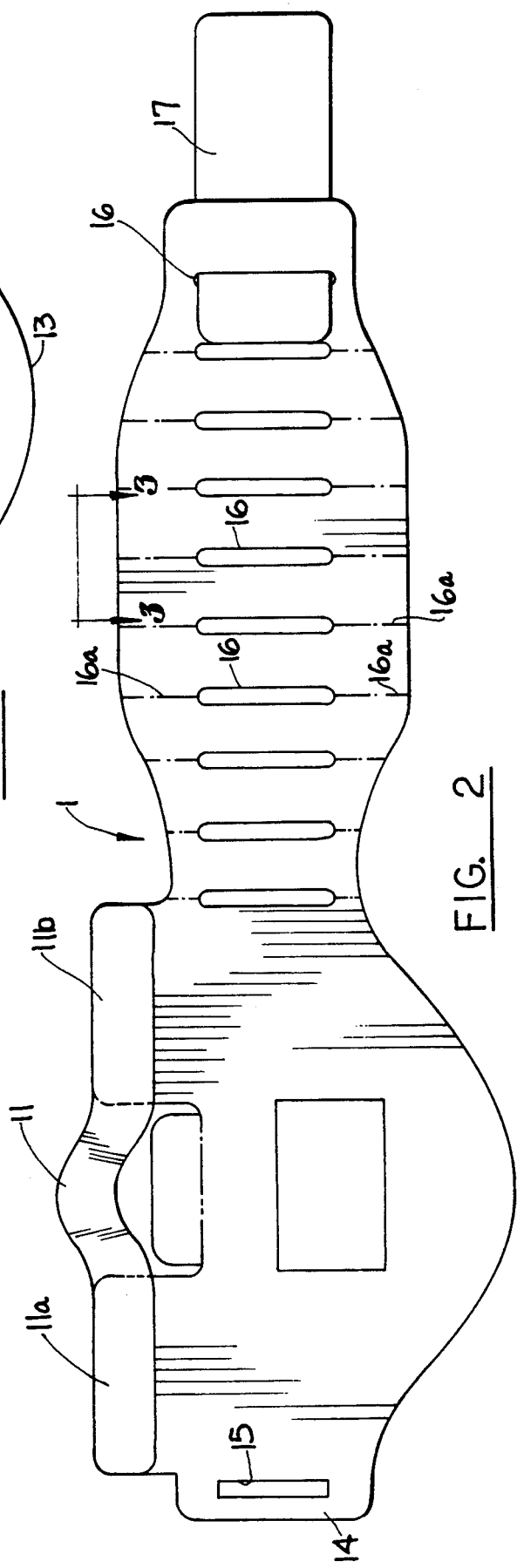

DISPOSABLE CERVICAL COLLAR

This invention relates to cervical collars adapted to be worn by persons with neck or spinal injuries, and more particularly relates to a disposable collar intended for one-time use.

BACKGROUND OF THE INVENTION

Numerous types of cervical collars have heretofore been proposed to limit the head and neck movement of a person suffering a neck or spinal injury. Cervical collars are now standard equipment for life squads and rescue units, and are normally intended for reuse, which means that the collar must be retrieved by the rescue squad personnel once removed from the injured person. In addition, and depending upon the nature of the injuries, the collar may become soiled or otherwise contaminated during use, and consequently may or may not be salvageable for reuse. In order to overcome these difficulties, the present invention provides an inexpensive disposable cervical collar intended for one-time use which nonetheless provides the necessary head and neck support for the injured person.

SUMMARY OF THE INVENTION

A cervical collar in accordance with the present invention comprises an essentially one piece elongated band adapted to be wrapped around the neck of the injured person, the band being configured to conform to the contour of the person's neck and the adjacent areas of the head and shoulders, with particular reference to those anatomical points which require immobilization.

In accordance with the invention, the collar is formed from a corrugated plastic material known as core board which is formed from polypropylene and is of a construction similar to conventional corrugated box board in that it has opposing surfaces interconnected in spaced apart relation by transverse webs which effectively define unidirectionally extending cells or compartments. The collar also may be formed from corrugated box board, although preferably it will be made from plastic core board, with the corrugations or cells extending vertically, i.e., from top to bottom of the collar. In either case, the collar will be compatible with x-rays, CT scans and MRI, as well as compatible with other types of rescue equipment, such as backboards and extrication devices.

The collar is configured to be quickly and easily applied in emergency situations and is adapted to be secured in the neck-enclosing position by means of a single flexible strap, preferably formed from a sheet of flexible plastic material, the strap being permanently secured to one end of the collar with its free end adapted to be adhesively secured to the opposite end of the collar once it has been fitted around the wearer's neck.

The collar is also configured to provide support for the wearer's jaws, which may include a plastic chin strap, the collar also having an opening beneath the chin supporting portion to permit ready access to the wearer's throat after the collar is in place.

In order to provide flexibility to the collar so that it may be easily wrapped around the wearer's neck, vertical score lines and slots are provided at spaced apart intervals to permit flexing or bending of the collar along predetermined lines of fold so that it may readily conform to the wearer's neck and adjoining areas of the chin and shoulders.

DESCRIPTION OF THE DRAWINGS

FIG. 1 is a top plan view of a cervical collar in accordance with the invention.

FIG. 2 is a rear elevational view thereof.

DESCRIPTION OF THE PREFERRED EMBODIMENT

Figure 3:
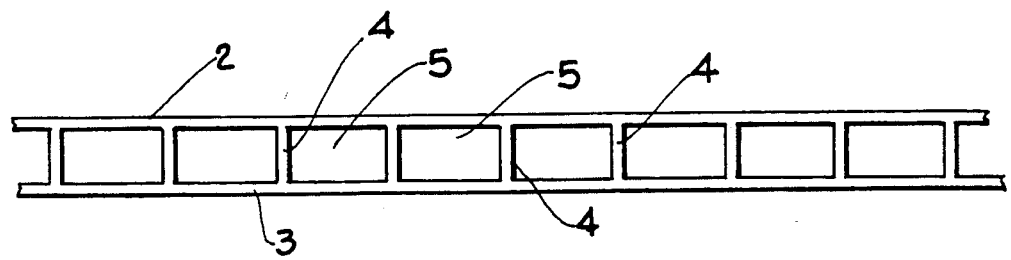
FIG. 3 is an enlarged fragmentary sectional view taken along the line 33 of FIG. 2.

Referring first to FIGS. 1 and 2, the cervical collar comprises an elongated body, indicated generally at 1, formed from a unitary piece of core board or similar cellular material having opposing surfaces 2 and 3, as seen in FIG. 3, interconnected at spaced apart intervals by transverse webs 4 to provide elongated cells 5 therebetween which extend vertically relative to the length of the elongated body 1. The cells act to provide rigidity to the collar, particularly in a direction transverse to the length of the collar.

The elongated body 1 may be conveniently die cut from a sheet of the corrugated material and comprises a frontal section 6 and a rear section 7 extending in lateral prolongation of the frontal section 6. Intermediate its upper edge, the frontal section 6 has a cut-out chin receiving opening 8 having an arcuate chin rest 9 extending upwardly from the lowermost edge of the opening 8 along a line of fold 10 which permits the chin rest to be folded outwardly relative to the plane of the frontal section. In the embodiment illustrated flexible plastic chin strap 11 bridges the opening 8, the chin strap being bowed outwardly relative to the plane of the elongated body so as to accommodate the wearer's chin when positioned on the chin rest 9, the opposite ends of the chin strap, indicated at 11a and 11b in FIG. 2, being secured to the rear surface of the frontal section 6 on opposite sides of the opening 8. The chin strap may be secured to the frontal section by an adhesive or by a heat sealing operation. Alternately, the chin strap may be eliminated, in which event the portions of the frontal section 6 lying to either side of the opening serve to engage and position the lower jaw.

The frontal section 6 is also provided beneath the chin rest with a cut-out opening 12 positioned to overlie the larynx as well as expose the wearer's neck in the event a tracheotomy is required.

The lower edge of the frontal section 6 is of curved configuration, indicated at 13, so as to seat against the wearer's chest in the area immediately beneath the neck. It may be noted that due to the formation of the collar from lightweight plastic materials, such as core board, the shape of the collar can be readily modified by simply cutting away parts of the collar where necessary.

Along its free side edge the frontal section 6 is provided with a tab 14 having an elongated slot 15 extending through one of the cells 5, the slot 15 serving along with the score lines 15a in the rear surface of the frontal section 6 to hingedly articulate the flap 14 relative to the adjacent edge of the frontal section 6. The rear section 7 of the elongated body is also provided with a series of spaced apart elongated slots 16 which are similar to the slot 15 in that they each extend through at least one of the cells 5 in the elongated body and effectively provide, together with the score lines 16a, lines of articulation by means of which the portions of the rear section 7 lying between the sets of slots and score lines may be folded relative to each other, thereby permitting the rear section of the collar to be wrapped around the rear portion of the wearer's neck. The slots 16 additionally serve to provide ventilation. In similar fashion the sides edges of the chin receiving opening 8 and the cut-out 12, which are in vertical alignment, effectively define lines of fold which permit the opposite sides of the frontal section 6 to contact and support the wearer's lower jaw.

At its free end the rear section 7 is provided with a flexible plastic strap 17 which passes through the outermost slot 16 with its innermost end adhesively secured to the rear surface of the rear section 7, as best seen in FIG. 2. When the elongated body is wrapped around the wearer's neck, the distal end of the strap 17 is secured to a stripe of pressure sensitive adhesive 18 applied to the tab 14 and the adjacent side of the frontal section 6, as seen in FIG. 1, the adhesive stripe 18 being protected by a removable release sheet 19 the corner of which is shown raised to illustrate the underlying adhesive stripe 18.

Figure 4:
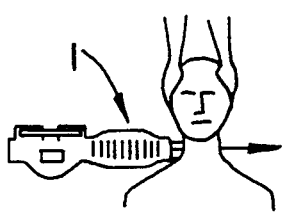
FIGS. 4, 5, 6 and 7 are sequential pictorial views illustrating the application of the collar to the neck of an injured person.
Figure 5:
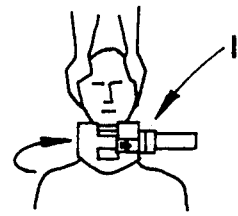
Figure 6:
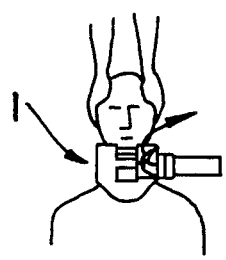
Figure 7:
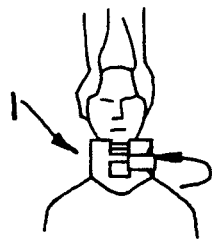

The mode of attachment of the collar is illustrated in FIGS. 4 through 7, the initial step, as seen in FIG. 4, being the positioning of the elongated body such that the rear section 7 will be centered relative to the rear of the wearer's neck, whereupon the collar will be folded so as to bring the frontal section 6 to the position illustrated in FIG. 5, with the wearer's chin projecting through the opening 8, the chin being seated on the chin rest 9, which folds forwardly, with the chin strap 11, if used, extending across and engaging the wearer's chin. As seen in FIG. 6, the release sheet 19 is next removed and the outermost end of rear section 7 folded about the opposite side of the wearer's neck with the strap 17 secured to the adhesive stripe 18, the collar thus assuming the position illustrated in FIG. 7.

It will be understood that the collar may be made in various sizes, such as small, medium and large, to accommodate children, as well as small and large adults, and may be color coded so that the sizes may be readily identified by rescue personnel. The collars may be stored in flat condition so that a supply of the collars may be stored in an ambulance or other rescue vehicle in a relatively small space.

It will be evident that modifications may be made in the invention without departing from its spirit and purpose. While a preference is expressed for a construction in which the elongated body and the straps are formed from plastic materials which are waterproof and nonabsorptive, other materials may be utilized, such as woven straps formed from plastic or textile strands. Similarly, the elongated body itself may be formed from corrugated box board rather than plastic core board, in which event it is preferred to coat the board with a water resistant material so that it will maintain its integrity, an essential requirement being that the body remain essentially rigid so as to provide the necessary neck and head support. Other forms of fasteners may be provided, such as Velcro fasteners, although adhesive is preferred due to its lesser cost and lack of added bulk.

What is claimed is:

1. A disposable cervical collar comprising a one piece elongated body formed from a sheet of a light weight material which is essentially rigid in a direction transverse to its length, said elongated body having opposing spaced apart surfaces interconnected by spaced apart webs defining elongated narrow cells extending transversely between the opposing side edges of said elongated body,
   said elongated body being configured to define a frontal section and a rear section connected to a side edge of said frontal section,
   a chin receiving opening extending downwardly from the upper edge of said frontal section centrally thereof,
   a second opening in said frontal section underlying said chin receiving opening,
   a plurality of spaced apart lines of articulation in said rear section along which said rear section will bend when the collar is fitted about the wearer's neck,
   a flexible strap projecting outwardly from the side of said rear section opposite said frontal section, and
   attachment means on the side of said frontal section opposite said rear section for securing said strap to said frontal section when the collar is fitted around the wearer's neck.

2. The disposable cervical collar claimed in claim 1 including a flexible chin strap bridging said chin receiving opening and secured to said frontal section adjacent said chin receiving opening.

3. The disposable cervical collar claimed in claim 1 wherein said chin receiving opening has opposing vertical side edges and a horizontal bottom edge, including a chin rest hingedly connected to the bottom edge of said chin receiving opening.

4. The disposable cervical collar claimed in claim 3 wherein said chin rest is integral with said frontal section.

5. The disposable cervical collar claimed in claim 1 wherein the attachment means for securing said strap to said frontal section comprises a stripe of pressure sensitive adhesive on the said frontal section, said adhesive stripe being covered by a removable cover sheet.

6. The disposable cervical collar claimed in claim 1 wherein the lightweight material from which said elongated body is formed comprises a plastic material.

7. The disposable cervical collar claimed in claim 6 wherein some at least of said lines of articulation in said rear section comprise narrow vertical slots each of which extends through at least one of said cells.

8. The disposable cervical collar claimed in claim 6 wherein some at least of said lines of articulation comprise score lines in said plastic material.

9. The disposable cervical collar claimed in either of claims 7 or 8 wherein said chin receiving opening and said second opening have their opposite side edges in vertical alignment, whereby to define lines of weakness to permit folding of said frontal section along the lines of weakness so formed.

10. The disposable cervical collar claimed in claim 1 wherein the lightweight material from which said elongated body is formed comprises corrugated boxboard.

11. The disposable cervical collar claimed in claim 10 wherein said boxboard is treated with a water resistant material.

* * * * *

UNITED STATES PATENT AND TRADEMARK OFFICE
CERTIFICATE OF CORRECTION

PATENT NO. : 5,060,637
DATED : October 29, 1991
INVENTOR(S) : K. Stephen Schmid, Richard A. Brault, Dianne B. Croteau, Jonathan P. Vinden It is certified that error appears in the above-identified patent and that said Letters Patent is hereby corrected as shown below:

Column 4 - Claim 1 - Lines 1-11 - These lines should be deleted and replaced with --A disposable cervical collar comprising a one piece elongated planar body having upper and lower longitudinal side edges, said elongated body being formed from a sheet of lightweight material which is capable of being readily cut and scored and has front and rear surfaces interconnected by spaced apart webs defining a continuous series of elongated narrow cells extending between the upper and lower longitudinal side edges of said elongated body, whereby said elongated body is essentially rigid in a direction transverse to its length, said elongated body being configured to define a frontal section and a rear section connected to an edge of said frontal section,--.

Signed and Sealed this

Ninth Day of March, 1993

*Attest:*

STEPHEN G. KUNIN

*Attesting Officer*   *Acting Commissioner of Patents and Trademarks*